United States Patent [19]

Kameda et al.

[11] Patent Number: 4,959,306

[45] Date of Patent: Sep. 25, 1990

[54] LABELING DESIGN FOR A BINDING ASSAY REAGENT

[75] Inventors: Naomi Kameda, Woodside; Gerald L. Rowley, San Jose, both of Calif.

[73] Assignee: Sclavo, Inc., Sunnyvale, Calif.

[21] Appl. No.: 935,952

[22] Filed: Nov. 28, 1986

[51] Int. Cl.$^5$ .................. G01N 33/53; G01N 33/563; G01N 33/531; G12N 11/06

[52] U.S. Cl. ........................................ 435/7; 435/181; 436/500; 436/501; 436/512; 436/519; 436/543; 436/544; 436/545; 436/546; 436/547; 436/823; 530/810

[58] Field of Search ............... 436/543, 544, 545, 546, 436/547, 532, 823, 500, 501, 512, 519, 801; 435/7, 181; 530/810

[56] References Cited

U.S. PATENT DOCUMENTS

| | | | |
|---|---|---|---|
| 3,853,987 | 12/1974 | Dreyer | 424/1 |
| 4,232,119 | 11/1980 | Carlsson et al. | 435/7 |
| 4,298,593 | 11/1981 | Ling | 436/512 |
| 4,423,143 | 12/1983 | Rubenstein et al. | 435/7 |
| 4,429,008 | 1/1984 | Martin et al. | 436/501 |
| 4,560,648 | 12/1985 | Armenta | 436/532 |
| 4,595,656 | 6/1986 | Allen et al. | 436/547 |

FOREIGN PATENT DOCUMENTS

| | | |
|---|---|---|
| 0077671 | 10/1982 | European Pat. Off. |
| 0155224 | 3/1983 | European Pat. Off. |
| 8404970 | 12/1984 | PCT Int'l Appl. |

OTHER PUBLICATIONS

Watanabe et al., Clin. Chem. vol. 25, 1979, p. 80-83.

Smith et al., Ann. Clin. Biochem., vol. 18, 1981, p. 253-274.

Jansen et al., Immunological Rev., vol. 62, 1982, p. 185-216.

*Primary Examiner*—Esther M. Kepplinger
*Assistant Examiner*—Florina B. Hoffer
*Attorney, Agent, or Firm*—Irell & Manella

[57] ABSTRACT

Methods and materials for preparing specific binding reagents with a multiplicity of relatively noninterfering label moieties are described. By spacing the labels at the surface of a specific reagent with bulking agent, increased sensitivity can be achieved without interference between individual labeling entities.

21 Claims, 5 Drawing Sheets

LABELING DESIGN FOR A BINDING ASSAY REAGENT

FIELD OF THE INVENTION

The invention relates to the determination of substances in biological or other samples using a binding assay, such as immunoassay, with labeled reagents. More particularly, it relates to a new design for labeled reagents which participate in the binding reaction in such assays. The general concepts involved in this design are illustrated by assays for T3, IgE and for ferritin.

BACKGROUND OF THE INVENTION

Techniques and protocols for assays involving immunoreaction of antigen/immunoglobulin moieties or other specifically binding moieties have been known for almost thirty years. One of the earliest disclosures of such protocols was the original radioimmunoassay procedure of Yalow. There are hundreds of specific assays and dozens of general protocols involved in such assays, whose unifying feature is that their specificity depends on the ability of the analyte in question, but not the contaminants accompanying it in the sample, to bind to the reagent.

Most frequently, the specific binding is an antigen/antibody immunoreaction and its variants, including the use of derivatives of immunoglobulins to bind to an antigen. The antigen, itself, may also of course, be an immunoglobulin. Other examples of specific binding, while perhaps less common, are nevertheless important, including the highly specific reaction between avidin and biotin, the attraction of particular lectins for certain proteins or glycoproteins, and so forth. The specificity need not be exquisite, as long as there are no interfering substances present in the sample which also bind to the reagent.

In broadest concept, the specific binding assays to which the designed reagents of the invention are applicable are conducted either in a direct or competitive manner. In a direct assay, the specific reagent is either itself labeled or provided a mechanism to acquire a label and used to bind to the analyte in the sample, thus removing it from the physical environment of the contaminants, or in some way changing its environment so that only its presence, among the associated materials in the mixture, is detectable. The amount of label associated with the analyte is then a direct measure of the quantity of analyte in the sample. Often a labeled antibody is employed for direct assays, in which case the assay is generally termed "immunometric".

Conversely, in the competitive approach, the analyte is caused to compete with itself in labeled form for the same specific reagent. The higher the concentration of competing analyte in the solution, the less label will be bound to the specific reagent. Thus, the amount of label associated with the specific reagent/analyte complex is in inverse proportion to the amount of analyte in solution.

The foregoing methods can be conducted as solid-phase assays, including sandwich assays, and may involve more than one specifically interacting substance in forming the final labeled conjugate.

Over the more than twenty years that this assay approach has been used, a number of labeling systems have come into common use, depending on the nature of the analyte, and the sensitivity required. The most common labels are radioisotopes, fluorescent materials, or enzymes capable of catalyzing detectable reactions. Radioimmunoassay (RIA), which employs radioisotopes as labels, generally is quite sensitive but, of course, is cumbersome to conduct due to the dangers associated with handling radioisotopes and the equipment involved in quantifying the radiation. Fluorescent labeling has been moderately less sensitive, a problem which might be overcome by increasing the number of dye molecules used as label, were it not for crowding effects resulting in the quenching of fluorescence due to the proximities of the fluorophores. Enzyme-mediated immunoassay techniques are also limited in sensitivity by the number of labeling enzyme molecules which can be crowded onto the specific reagent. The problem of fluorescence quenching with multiple labels is serious enough to diminish the sensitivity of assays using this approach. Concentration quenching with multiple labels is discussed in, for example, Smith, D. S., et al, *Ann Clin Biochem* (1981) 18:253. Thus, it would be desirable to utilize a method of labeling which permits enhancement of sensitivity by permitting multiple labels, which still retain their effectiveness, to be attached to the specific reagent. The present invention, by designing a method and final product to achieve efficient multiple labeling, provides the opportunity to maximize the practicality of labeled specific analytical binding reactions.

DISCLOSURE OF THE INVENTION

The invention relates to techniques for labeling specific reagents useful in analytical applications and to the resulting labeled reagents. The design permits the use of a multiplicity of label in association with a single molecule of specific reagent without the disadvantages normally encountered in directly labeling such reagents with more than one or several labeling entities. In particular, the problem of fluorescence quenching is overcome.

In one design, the specific reagent, which might be, for example, an antigen or antibody, is provided with a multiplicity of bulking groups which contain only one site capable of forming the linkage to join them to the reagent. The bulking agent moieties have one or more labels covalently attached.

Thus, in one aspect, the invention relates to specific binding reagents having a binding moiety conjugated to at least one, preferably a multiplicity of, bulking agents, to which, in turn, are bound one or more labeling groups. In other aspects, the invention relates to methods to prepare the reagents of the invention and to methods to analyze samples employing them.

MODES OF CARRYING OUT THE INVENTION

A. Definitions

Figure 1A:
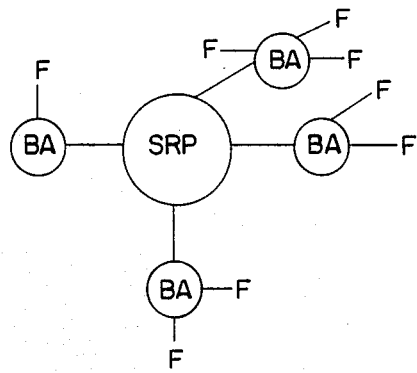
FIG. 1A shows a diagram of a preferred generic design of the reagent of the invention.

As used herein, "substance specifically reactive with analyte" refers to a substance which is capable of reacting with whatever comprises the analyte, but not with contaminants under the conditions of the assay. This substance is most commonly a component of an antigen-/antibody reaction; it can either be the antigen or the antibody. The immunospecific substance may be either a complete immunoglobulin or antibody specific for the antigen, or may be an "immunospecific portion thereof", such as the F(ab')$_2$ fragment, or other portion of the antibody that reacts specifically with antigen. The antigen can be any of a variety of materials, including immunoglobulin or fragments thereof. It may be a protein, a carbohydrate, or any molecule of sufficient size to constitute an antigenic determinant. Antibodies, in general, can be raised against sites of approximately 10 Å or more if the materials comprising such sites are sufficiently large or are made sufficiently large to be immunogenic by conjugation to carrier molecules. This is frequently the practice in generating antibodies to, for example, smaller peptide units or other small molecules in specific vaccines.

The "substance specifically reactive with analyte" also refers to the components of reactions which are not immunoreactions, but which retain the property of specificity in the face of contaminants. For example, certain lectins react specifically with the carbohydrate moieties on certain proteins, certain receptors found on cell surfaces react specifically with their target materials; biotin reacts specifically with avidin. Thus, "substance specifically reactive with analyte" is used as a general term to indicate the other partner in an affinity reaction between an analyte substance and a substance specifically reactive with it, including, but not limited to, antibody and a material containing an antigenic determinant for which it is specific.

More general than a "substance specifically reactive with analyte" is a "specific reaction partner" (SRP) which term may refer either to the above substance reactive with analyte or to the analyte itself. Each is the counterpart of the other in the highly specific interaction which forms the basis for the assay.

Also, the term "specific reaction partner" refers to the substance accounting for the specificity in either labeled or unlabeled form, as will be clear from the context.

"Label" refers to a moiety which accounts for the detectability of a complex or reagent. In general, the most common types of labels are fluorophores, chromophores, radioactive isotopes, and enzymes.

"Fluorophore" (F) refers to a substance or portion thereof which is capable of exhibiting fluorescence in the detectable range. Typically, this fluorescence is in the visible region, and there are common techniques for its quantitation. Examples of fluorophores which are commonly used include fluorescein, (usually supplied as fluorescein isothiocyanate [FITC]), rhodamine, dansyl, and umbelliferone.

"Bulking agents" (BA) are also designated spacer proteins (SP). These refer to molecules which are not themselves specific with regard to the participants in a reaction specific for analyte, but which are molecules of sufficient size that they can effectively be used as bulky linkers between specific portions of the reagent and the label. Depending on the specific components of the reaction, the workable size for the bulking agents can vary widely. However, in general, for most applications, the bulking agents of the invention should have a molecular weight on the order of 1-2000 kd, preferably 20-100 kd. These sizes cover the majority of cases, and represent the most generally useful range. However, no definite outer limits can be set, and in any particular instance smaller or larger bulking agents than those here suggested may be desirable. In order to be operable in the preferred method of the invention for preparation of the labeled reagent, the bulking agent should have only one functional group which is reactive with a particular functional group on a heterobifunctional linker. Particularly preferred is a sulfhydryl group. As illustrated below, a particularly useful bulking agent is an Fab' fragment of rabbit IgG since not only is this of an approximately correct molecular weight, but it also contains one and only one sulfhydryl group, which can then be used to bind specifically to heterobifunctional linkers designed to form thioethers or disulfide linkages.

B. General Description of a Preferred Embodiment of the Invention

Figure 1B:
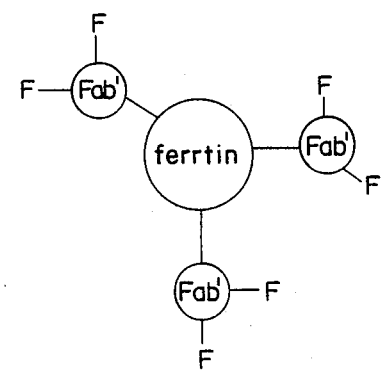
FIG. 1B shows an embodiment using ferritin as specific reaction partner.

In general, the preferred compositions of the invention have the configuration shown in FIG. 1 both in the general and for the particular case of ferritin. In this design, the specific reaction partner is linked to a multiplicity of bulking agents. The bulking agent in turn is linked to one or more labels. The ratio of bulking agent to specific reaction partner is variable, and to some extent depends upon the analyte being tested. For labeling of specific reaction partners which are relatively low in molecular weight, such as T3, only one bulking agent per reagent molecule may suffice. In this case, presence of the bulking agent prevents the fluorophore from being in the proximity of the iodide moiety of T3; iodide is a known quencher. However, for larger reagents, more bulking agent may be used to increase sensitivity. The upper limit also depends, of course, on the size of the specific reaction partner. For example, for fluorescent labeling of ferritin, an advantageous range is approximately 5-14, the lower limit being set to assure sufficient sensitivity and the upper limit being set to prevent unacceptable overcrowding of the label.

Appropriate and preferred procedures to put together a reagent of the type shown in FIG. 1 are described below. In order for this preferred procedure to be effective, the bulking agent must contain only one functional group capable of reacting with linker, and a heterobifunctional linker is required.

The bulking agent is first labeled with the desired labeling material by a convenient chemical reaction appropriate to the choice of components. For example, the amino groups of the bulking agent may be used to bind with the commonly used fluorescent compound fluorescein isothiocyanate (FITC). In this case the stoichiometry of label to bulking agent is controlled by the relative amounts of materials added to the reaction mixture. The resulting labeled bulking agent is then linked through a heterobifunctional linker to the specific reaction partner.

This can be achieved in two alternative ways. The linker can be put first on the specific reaction partner (SRP) after protecting or blocking, if necessary, alternate groups which would react with the other end of the bifunctional linker. Alternatively, the linker is first bound to the bulking agent, again preliminarily protecting or blocking any groups on the bulking agent, which would otherwise react with the other functional group on the linker. The SRP or bulking agent (BA) bearing the linker is then conjugated to its opposite member, taking advantage of the reactivity of the other group on the linker.

In one specific illustration, the heterobifunctional linker contains sulfhydryl-binding functional groups at one end, for reaction with a bulking agent, such as rabbit IgG Fab' fragment containing only one sulfhydryl group and a labile group at the other, such as an active ester. This set of functional groups mandates a certain sequence of reactions to link the bulking agent to SRP. For example, a frequently used linker, sulfo-SMCC, contains a highly labile ester reactive with the amino groups of a protein substrate as one functional group and the sulfhydryl-binding group as the other. The ester groups must be reacted with protein substrate first. This is in order to prevent hydrolysis and inactivation of the functional group during reaction with the opposite, sulfhydryl-reacting end of the molecule. Accordingly, in this case, the linker is first linked to SRP by virtue of the labile ester linkage, having first protected the sulfhydryl groups of SRP, if necessary, using, for example, iodoacetate or N-ethylmaleamide (NEM), as illustrated below. The SRP-containing linker is then reacted with the single sulfhydryl group on the Fab' fragment to complete the reagent.

However, this sequence is mandated only by the specific nature of the functional groups on the heterobifunctional linker. Should a linker have been used having, for example, instead of an N-hydroxysuccinimide ester (active ester) group for reaction with the amino side chains, an azide functional group, which requires activation by light in order to become reactive, the linker could have been bound to the bulking agent through the sulfhydryl linkage first, and then the linker-modified bulking agent used to react with the SRP.

It should also be noted that the use of a linker to obtain the preferred configuration of the invention is not always necessary. For example, a bulking agent containing a single—SH group could be "activated" with a sulfhydryl activating agent—e.g., by reaction with 5,5'-dithiobis-(2-nitrobenzoic acid)—to obtain a reactive disulfide capable of binding to available—SH groups in the SRP.

Figure 1C:
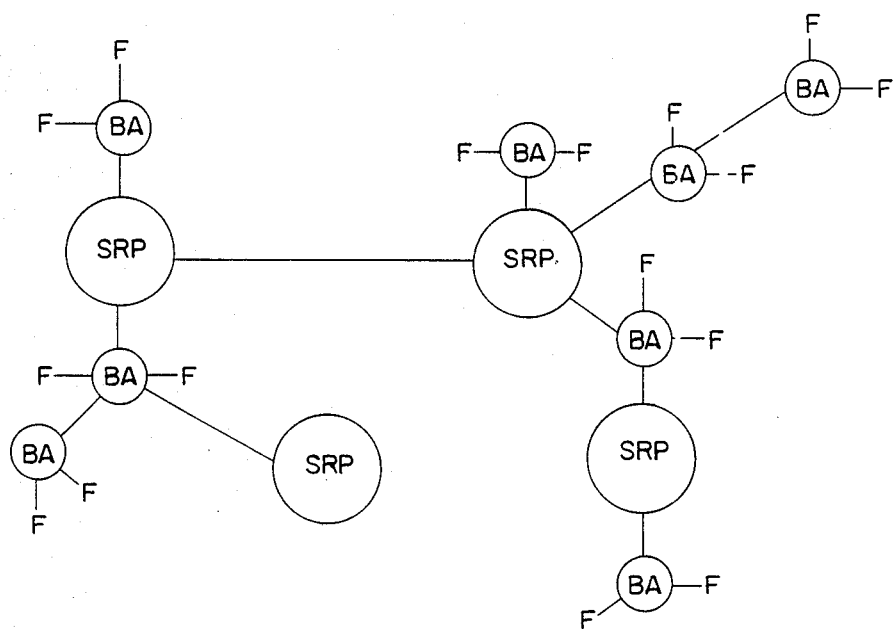
FIG. 1C shows a less preferred randomly bonded form.

Furthermore, homobifunctional linkers and permissive reaction stoichiometries can be used to obtain composites which are less preferred, but nevertheless workable, forms of the reagents the invention. Complexes wherein bonds between individual BA molecules exist, or wherein a BA molecule is linked to more than one SRP, can also be used and may exhibit decreased quenching. Such a "random" configuration is shown in FIG. 1C. In such cases, also, a dehydrating agent, such as a carbodiimide, e.g. ethyl carbodiimide or dicyclohexyl carbodiimide, can be used to obtain an amide bond linking the BA directly to the SRP.

C. The Components of the Reagent Compositions

The nature of the various components the compositions of the invention depends, of course, on the analyte and on the protocol selected. If a competition assay is to be run, the SRP to be labeled according to the method of the invention corresponds to, i.e., is equivalent to or is the same compound as the analyte itself. If noncompetitive, immunometric assay methods are to be used, the labeled SRP is either itself directly reactive with the analyte or reactive with an intermediate material which is specifically reactive with the analyte.

Thus, for competition reaction, suitable SRP moieties include analytes commonly assessed in biological fluids, such as, for example, any of a variety of enzymes, including G-6-P, alkaline phosphatase, hexokinase, catalase, alcohol dehydrogenase, and so forth; various hormones, such as luteinizing hormone, follicle-stimulating hormone, thyroid-stimulating hormone, human chorionic gonadotropin, thyroxin derivatives (T3 and T4), ferritin, particular immunoglobulins; small molecules such as theophylline, diazepam, penicillin, and tetracycline, against which antibodies could raised; biotin; legal or illegal drugs; virus proteins; and so forth.

If the protocol is that of a noncompetitive (direct) assay, the SRP might well be an antibody or portion thereof specifically reactive with any of the analytes such as those listed above, or the specific reaction partner may be reactive simply with another intermediate specific reaction partner. For example, if the protocol is designed to detect the presence of human chorionic gonadotropin (HCG) using mouse antibodies specific against HCG as a primary reagent, the labeled reagent might be, for example, rabbit anti-mouse IgG.

The bulking agent is, generally, a polymer of molecular weight of at least approximately 1 kd, and an upper limit which depends on the size of the SRP and the number of bulking agents intended to be crowded around the specific reagent portion of the finished composition. Of course, if the size of the BA compared to the SRP is too large, the number of BA which can be attached without overcrowding is quite limited. In order to provide for efficient preparation, the bulking agent should contain only one functional group capable of reacting with a particular functional group on the end of a heterobifunctional linker. For example, proteins containing only one side-chain amino group might be used, or a polymer of glycine might be used, provided conjugation to label could be achieved through, for example, the amino or carboxy terminus. Alternatively, polymers providing a limited number of functional groups for binding of label might be used, such as a 10:1 mixture of glycine with cysteine. The -SH groups of the cysteine residues could then be used to bind to label, while the attachment to linker is through either terminus, or 10:1 mixture of lysine with cysteine; the amino groups bind to label and -SH to linker. A particularly preferred BA might be polyproline, as it exhibits a singularly stable spacer function.

A particularly convenient bulking agent is the Fab' fragment of, for example, rabbit immunoglobulin since it contains one sulfhydryl group, a common functional group for reactivity with commercially available bifunctional linkers. This fragment is prepared by means well known in the art by treating immunoglobulin with pepsin, thus yielding the F(ab')$_2$ fragment, followed by treating with reducing agent to reduce the single disulfide bond and thus produce two Fab' portions. Other suitable and preferred peptides which are known to contain only one -SH group include mercaptoalbumin and human α1-antitrypsin. Of course, any protein or peptide containing a single instance of a type of reactive functional group would be suitable.

Groups suitable for labels are multitudinous and well known in the art. Useful labels containing radioactivity include $I^{131}$, $I^{125}$, $Ce^{137}$, and $P^{32}$. Suitable fluorescent labels include fluorescein, dansyl, and rhodamine, and so forth. Chromophores are less convenient because their detection is less sensitive, but nevertheless are included within the scope of the invention, and include a large variety of compounds known in the art for dyeing fabrics, for example. Suitable enzyme labels include horseradish peroxidase, glucose dehydrogenase, glucose oxidase, and diaphorase. A large number of suitable labels are known to those practicing the art and are readily available to them.

Heterobifunctional (and homobifunctional) linkers are also commercially available and include, generally, those reactive with sulfhydryl groups or amino groups of proteins. Particularly popular are SMCC and SPDP and their water soluble sulfo forms, as explained below. A representative list of functional groups contained in such heterobifunctional linkers includes activated esters, such as imidates, azides, and activated disulfides.

There are a large number of heterobifunctional agents which generate a disulfide link at one functional group end and a peptide link at the other, and these have been used extensively. One of the most popular of these is N-succinimidyl—(2-pyridyldithio) propionate (SPDP). This reagent creates a disulfide linkage between itself and a cysteine residue in one protein and an amide linkage through the amino on a lysine, or other free amino group in the other. A variety of such disulfide/amide forming agents are known. See for example, *Immun. Rev.* (1982) 62:185. Other bifunctional coupling agents form a thioether rather than a disulfide linkage. Many of these thioether forming agents are commercially available and include reactive esters of 6-maleimidocaproic acid, 2-bromoacetic acid, 2-iodoacetic acid, 4-(N-maleimidomethyl) cyclohexane-1-carbolic acid and the like. The carboxyl groups can be activated by combining them with succinimide or 1-hydroxy-2-nitro-4-sulfonic acid, sodium salt. A particularly preferred coupling agent for the method of this invention is succinimidyl 4-(N-maleimidomethyl) cyclohexane-1-carboxylate (SMCC) obtained from Pierce Company. Rockford, IL. Some of these representative compounds may be rendered water soluble by addition of a hydrophillic group, such as, for example, a salt of sulfonic acid substituent. The foregoing list is not meant to be exhaustive, and modifications of the named compounds can clearly be used.

Other coupling agents that may be used are various bifunctional derivatives of imidoesters such as dimethyl adipimidate HC1, active esters such as disuccinimidyl suberate, aldehydes such as glutaraldehyde, bis-azido compounds such as bis(p-azido-benzoyl)hexanediamine, bis-diazonium derivatives such as bis-(p-diaoziumbenzoyl)-ethylene diamine, diisocyanates such as tolylene 2,6-diisocyanate, and bis-active fluorine compounds such as 1,5-difluoro-2,4-dinitrobenzene.

In a typical, preferred approach, a thioether linkage is formed between a sulfhydryl on the BA portion of the conjugate and the coupling agent and an amide linkage is formed between an $\epsilon$-$NH_2$ of a lysine contained in the SRP and the carboxyl of the coupling agent.

D. Proportion of Components and Properties of the Composition

The compositions of the invention have certain unexpected properties. For example, in many instances, the antigenic reactivity of the SRP in the specific reaction is better preserved in constructing a labeled moiety according to the invention rather than by conventional direct labeling. Loss of reactivity due to labeling is apparently diminished by the use of bulking agent. This appears to be true for T3 as SRP, and there are data below demonstrating this for IgE as SRP.

Since the reagent compositions contain multiple labels on their surface, the sensitivity of the assay is dramatically increased, and increases even over directly labeled SRP with multiple labels. This is because the proximity of the labels, when directly attached, causes fluorescence quenching in the case of a fluorescent label, thus obviating the advantage of increased sensitivity; or, in the case of an enzyme label, negatively impacts the activity of a particular labeling enzyme due to overcrowding. Thus, the reagents constructed according to the method of the invention offer increased effectiveness in the specific reaction binding capability, and also increased sensitivity.

To achieve these ends, the ratio of label to bulking agent and of bulking agent to SRP is clearly important. A few general guidelines as to the optimum proportions can be given, although, of course, the most advantageous proportions are highly dependent on the nature of the components chosen for a particular embodiment.

In general, the proportions are regulated by the considerations set forth hereinabove. For ferritin or for IgE, the preferred ratio of Fab' to SRP is 5–14. Ratios greater than 14 lead to overcrowding and therefore to occultation of binding sites; ratios less than 5, at least in fluorescence assays, lead to reduced sensitivity. For T3 as the SRP, however, because of its small size, a ratio of Fab'/T3 of 1 is preferred.

When fluorescein is used as the label in the IgE. T3, or ferritin assays, ratios of fluorescein/Fab' of 1–6, or preferably 1–4.5, or more preferably 1.5–2.5, are used. The preferred ratios offer the optimum balance between the maximum number of fluorescence molecules and the minimum amount of quenching.

The method of constructing the compositions described is advantageous in minimizing side reactions. It is, of course, possible to synthesize the compositions of the invention using other protocols, such as employing homobifunctional linkers for the binding of SRP to BA. However, this requires that the particular product mixture which contains the desired composition be isolated from mixtures which will also contain SRP linked to SRP. BA linked to BA, and polymeric mixtures of each and both components.

In addition, of course some of these may be satisfactory, and separation may not be necessary.

E. Use of the Compositions of the Invention

The invention compositions are used in standard immuno or other binding assays in ways dictated by the nature of the specific reaction partner and the label, according to methods known in the art. Specific methodologies are illustrated below. These are meant for illustration only, and other specific compositions and other specific protocols which fall within the scope of the invention will be known to those in the art.

F. The Ferritin Assay

Ferritin is the major intracellular storage source of iron which can be mobilized as required and transported bound to the blood protein, transferrin. Apoferritin has a molecular weight of 440 kd and contains 24 protein subunits arranged as a spherical shell. When iron is bound under physiological conditions, ferritin consists of a heterogeneous population of molecules which contain 0–4500 iron atoms per entity. Ferritin is synthesized in the intestinal mucosa, liver and spleen in response to dietary intake. Although most of the ferritin pool is intracellular, small but significant amounts are found in the blood, and increased serum ferritin levels have been related to the presence of certain diseases such as hepatic necrosis, malignancy, and severe inflammation. In the absence of these or other abnormal conditions, serum ferritin is secreted in constant proportion to the total iron stores. Quantitative determination of serum ferritin has thus become useful for monitoring iron storage levels in blood donors and in patients undergoing hemodialysis. Evaluation of serum ferritin levels also permits differentiation between iron-deficiency anemia and other forms of anemia.

Other assays for ferritin include radioimmunoassay (RIA) (Miles, L.E.M., et al *Anal Biochem* (1974) 61:209; Luxen. A. W.. et al. *Clin Chem* (1977) 23:683) and enzyme-linked immunosorbent assay (ELISA) (Watanabe, N., et al, *Clin Chem* (1979) 25:80; Conradie J. D., et al, *S Afr Med J* (1980) 57:282). There have been no reported procedures for fluorescence-labeled immunoassay of ferritin, to Applicants' knowledge.

In conducting the assay, the biological sample is mixed with an antibody preparation reactive with ferritin and the labeled ferritin composition of the invention. Preferably this is done sequentially—i.e., the antibody preparation is mixed first with sample and, after incubation, with the labeled ferritin reagent of the invention. The invention composition effectively competes with the analyte ferritin for the anti-ferritin antibody; if the protocol is sequential, the sample ferritin will equilibrate with antibody before addition of competition. The immunocomplexes are then separated from the remainder of the sample by any of a number of protocols, including addition of an immunoprecipitant or by having provided the antibody on a solid support. The isolated immune complex is then dissolved to obtain a fluorescence reading or is read directly as a solid, or the fluorescence remaining in solution after separation of the complex is used as a measure of the ferritin in the sample.

G. IgE Assay

IgE is a class of immunoglobulin diagnostic for prediction of allergic reaction in children and in confirming suspected allergic diseases. Studies have shown that allergic conditions such as asthma, hay fever, and eczema result in IgE levels 3-10 times the normal level. Also, elevated serum IgE levels have been found in patients with parasitic disorders and in patients with certain types of cancer.

IgE has a molecular weight of approximately 196 kd and consists of two light chains and two heavy chains bound by disulfide bonds and noncovalent interactions. It can be quantitated in biological samples using RIA competitive binding (Johansson. S.G.O., *J Clin Path* (1968) 28 Suppl: 33) or by other solid-phase RIA techniques (Johansson S.G.O., et al. *Immunol* (1968) 14:265: Hussain, R., et al. *Am J Trop Med Hyg* (1983) 32:1347), or by ELISA (Engvall et al, *Immunochem* (1971) 8:871). The procedure is conducted in a manner analogous to that set for for ferritin above except that the SRP in the composition is IgE rather than ferritin.

EXAMPLES

The following examples are meant to illustrate the invention and should not be construed to limit its scope.

Preparation A: Preparation of 5-Fluoresceinylthioureidoacetic Acid t-butyl Ester To a 50 ml round bottom flask equipped with magnetic stirring bar was added a solvent mixture (10 ml THF, 5 ml of CHCl$_3$, and 5 ml of DMF) and 168 mg (1 mmole) of glycine t-butyl ester hydrochloride. The solution was cooled by an ice-water bath and 415 ml (3 mmoles) of triethylamine was added. To the above mixture was added FITC (fluorescein isothiocyanate, 1 mmole, 385 mg) in small portions over 3 hours. The reaction mixture was allowed to stir overnight and then concentrated to a red-brown oil that was dissolved in 100 ml ethyl acetate and washed with 5 ml water followed by 2–10 ml portions of saturated brine. Preparative tlc on silica with 10% methanol in chloroform and a trace of acetic acid gave tlc pure material, 240 mg. Molar extinction coefficient: $\epsilon = 79,500$ M$^{-1}$cm$^{-1}$ ($\lambda$max=494 nm) in 0.5 M sodium carbonate, pH 9.53. Anal. calc for $C_{27}H_{24}N_2O_7S \cdot H_2O$: C, 60.22; H, 4.83; N, 5.20; S, 5.95. Found: C, 60.16; H, 4.85; N, 5.01; S, 6.15.

Example 1

Preparation of Apoferritin Reagent

As described in detail below, the apoferritin reagent prepared in this example contains apoferritin surrounded by and covalently linked Fab' fragments which are labeled with fluorescein. The ratio of fluorescein/Fab' is 1.6. The ratio of Fab' groups to ferritin is 5.0.

Preparation of Apoferritin with a Multiplicity of Linker

Human liver ferritin was first reduced and dialyzed to remove iron and then reacted with N-ethylmaleimide (NEM) to inactivate sulfhydryl groups. 1.1 mg human liver ferritin in 0.36 ml buffer was dialyzed against 3×300 ml portions of 0.10 M sodium acetate. 0.10 M thioglycolate, pH 4 4. over 6 hr at room temperature, and dialysis then continued against 3×300 ml portions of 0.15 M potassium chloride, and then followed by 3×300 ml portions 20 mM sodium phosphate. 1 mM EDTA, pH 6.0, with changes every 2 hr.

The dialyzate, containing apoferritin (0.42 ml) was treated with NEM by adding, slowly with rapid stirring, 8.4 µl of 50 mM NEM in dimethylformamide (DMF). The resulting clear solution was incubated overnight at 25–30° C.

The solution was then adjusted to pH 7.0 by slow addition of 7 µl 0.50 M sodium carbonate, pH 9.5. A solution of sulfo-SMCC (Pierce Chemical Co.), 5 µl, 35 mM in dry DMF, was added slowly with rapid stirring in an ice bath, and after addition was complete, the resulting solution was incubated at 30° C. for 90 min. Unbound NEM and sulfo-SMCC were removed by gel chromatography on a 1×10 cm Sephadex-G 25 column eluted with 0.1 M sodium phosphate. 5 mM EDTA, pH 6.0. The protein-containing fractions were pooled and shown to contain linker to ferritin at a ratio of 8.0 by reacting a 200 µl aliquot with standardized mercaptoethanol solution and back-titrating of unreacted mercaptoethanol with 5,5'-dithiobis-(2-nitrobenzoic acid).

Preparation of Fluorescein Labeled Fab' Fragments

Rabbit F(ab')$_2$ available commercially or readily synthesized from rabbit IgG using pepsin digestion was first converted to Fab' by treating with reducing agent. A 16 μ portion of 1.1 M cysteamine hydrochloride solution was added in 3 equal portions to 1.6 ml of a solution containing 20 mg rabbit F(ab')$_2$ in 100 mM sodium phosphate. 5 mM EDTA, pH 6.0, with stirring over a 3 min period. The resulting clear solution was incubated at 37° C. for 2 hr and then dialyzed for 1 day against 6×100 ml buffer changes at 4° C. A 538 μl aliquot of the above solution was adjusted to pH 8.9 using an equal quantity of 0.5 M sodium carbonate, pH 9.4, and the resulting solution put into a capped, argon-flushed vial with a magnetic stir bar. A freshly prepared solution of FITC (44.9 μl in 0.5 M sodium carbonate, pH 9.4) was then added, and the resulting solution stirred for 77 min at room temperature in the dark. The reaction was stopped by the addition of about 3 mg solid glycine. The sample was then chromatographed on 0.7×18 cm Sephadex G-25 column prewashed with 1 M propionic acid and equilibrated with pH 6.0 buffer. Fractions containing 3 drops each were collected, and fractions 25-39 containing labeled protein were pooled and dialyzed against pH 6.0 buffer to remove remaining glycine.

The resulting labeled Fab' fragments were shown to contain a fluorescein/Fab' ratio of 1.6 by ultraviolet spectroscopy. The Fab' thiol groups were also titrated with 5,5'-dithiobis(2-nitrobenzoic acid). and it was shown that 0.63 SH moieties per mole Fab' were present.

Completion of the Reagent

A 302 μl sample of the fluoresceinated Fab' prepared above, containing 14.0 nmoles thiol was added to 1.70 ml of the apoferritin conjugated to the multiple linker moieties prepared above. This provided 7.00 nmoles of bound linker. The reaction was allowed to run overnight (15 hr) at room temperature. A small amount of insoluble solid was removed by centrifugation, and the supernatant was applied to a 1×35 cm Ultrogel AcA 22 column to remove unbound fluoresceinated Fab'. The column was eluted with 50 mM sodium phosphate, 0.1% sodium azide pH 7.5, and 8-drop fractions were collected. The fractions in the center of the first protein peak containing the desired complex were pooled.

The resulting complex was shown to contain 5.0 labeled Fab' fragments per ferritin by ultraviolet spectroscopy and BCA (pierce Chemical Co.) protein analysis.

Example 2

Preparation of IgE Reagent

The complex analogous to that in Example 1, but containing IgE as specific reaction partner, was prepared according to the procedure set forth in this example. The resulting complex contained 5.9 fluoresceinated Fab' moieties per IgE. The fluorescent labeling per Fab' fragment was approximately as in Example 1 (2.0 fluorescein/Fab').

Conjugation of IgE to Linker

A solution of 2.50 mg human IgE in 0.97 ml buffer was dialyzed against 4×1000 ml portions of 100 mM sodium phosphate. 5 mM EDTA, pH 6.0, over 2 days at 4° C. No blocking of thiol groups was necessary, as the IgE putatively contains no free sulfhydryl groups. Thus, the dialyzed IgE (0.89 ml) was treated with 21.3 μl of a 63 mM solution of sulfo-SMCC in dry DMF over 42 min with rapid stirring in an ice bath. The resulting clear solution was incubated at room temperature for 2 hr and unbound sulfo-SMCC removed by gel chromatography on 1×14 cm Sephadex G-25 columns eluted with 100 mM sodium phosphate, 5 mM EDTA, pH 6.0. The fractions at the center of the protein peak were pooled, and the number of bound linker moieties determined as described in Example 1. In this preparation, the resulting complex contained 8.6 moles linker/mole IgE.

Preparation of Labeled Reagent

The fluoresceinated Fab' fragment, prepared as in Example 1 but containing a ratio of fluorescein/Fab' of 2.0, was bound to the linker-conjugated IgE as follows. A 2.68 ml sample of fluoresceinated Fab' containing 202 nmoles thiol was added to 1.64 linker-conjugated IgE solution containing 65.6 nmoles linker and incubated for 4 days (90 hr) at room temperature. The small amount of insoluble material formed was removed by centrifugation and the supernatant was applied to a 1.5×50 cm Ultrogel AcA 34 column to remove unbound fluoresceinated Fab'. The column was then eluted with 100 mM sodium phosphate, 5 mM EDTA, pH 6.0, buffer. The central portions of the first protein peak were pooled and assayed for the number of fluoresceinated Fab'/IgE by ultraviolet spectrosoopy and BCA protein analysis. This ratio was shown to be 5.9 labeled Fab'/IgE.

Example 3

Relative Quantum Efficiency and Antigenic Reactivity of IgE Conjugates

The IgE compositions prepared in Example 2 containing a ratio of fluorescein/Fab' of 2.0 and Fab'/IgE of 5.9 were compared with respect to quantum efficiency and antigenic efficiency with IgE directly labeled by treating with FITC. The comparison FITC-treated IgE was shown by UV spectroscopy and BCA protein analysis to contain 10.3 fluorescein/IgE.

Solutions were made containing $1\times10^{-10}$ M fluorophore of either the IgE directly labeled or the conjugate of Example 2. Fluorescence was read on a standard Immpulse ® fluorometer manufactured by Sclavo Inc. West Coast (Sunnyvale, CA) and compared to the fluorescence output of a model compound, 5-fluoresceinyl-thioureidoacetic acid t-butyl ester, (Preparation A), which was given an arbitrary value of 1.0. The relative quantum efficiency on this scale for the directly labeled IgE, containing 10.3 fluorescein/IgE, was 0.587. The complex of the invention, containing a calculated value of 11.8 fluorescein/IgE, had a relative quantum efficiency of 0.901; almost twice as high.

In addition, the antigenicity of these materials was measured using IgE radioimmunoassay (Kallestad) and compared to the antigenic reactivity of unconjugated IgE, which was set at a value of 1.0. Both complexes lost antigenic reactivity, but the conjugate of the invention was 2.6 times as antigenic as the directly labeled fluorescein conjugate. The directly labeled IgE showed a relative antigenic as the 0.144, while the composition of the invention has a relative antigenic reactivity of 0.371.

Example 4

Preparation of Labeled T3 Reagent

The preparation of T3 also follows the general pattern of the foregoing examples.

Conjugation of T3 to Linker

To a solution of 3,3',5-triiodo-L-thyronine sodium salt (0.45 mmoles, 303 mg) in 10 ml of DMF and 70 μl of triethylamine (0.5 mmoles) under an argon blanket was added succinimidyl 4-(N-maleimidomethyl) cyclohexane-1-carboxylate (SMCC. 0.5 mmoles, 167 mg) in portions over one hour. The reaction was allowed to stir for an additional four hours and the solvent was removed under reduced pressure. A solution of 10 ml of $H_2O$, 1 ml of saturated brine, and a few drops of 6 N HCl, pH 3, was added to the residue, and it was extracted with 175 ml of ethyl acetate. The organic layer was washed by 2×20 ml portions of saturated brine and dried ($Na_2SO_4$). Removal or the solvent under reduced pressure gave an oil.

Purification by preparative tlc on silica ($CHCl_3$:MeOH:HOAc=80:20:trace) gave 67 mg of purified product. Recrystallization from ethyl acetate-cyclohexane gave 50 mg of pure T3-linker product—i.e., N-(4-(N'-maleimidomethyl cyclohexane-1-carboxyl) 3.3',5-triiodo-L-thyronine. Infrared and nuclear magnetic resonance spectra were consistent with the structure. Microanalysis for $C_{27}H_{25}N_2O_7I_3$: Calc.: C, 37.24: H, 2.87; N, 3.22; I, 43.78. Found: C, 38.05; H, 3.09; N, 3.14; I, 44.10.

Completion of Reagent

Fluoresceinated Fab' (fluorescein/Fab'=2.1), 10.6 mg, in 2.3 ml 100 mM phosphate, 5 mM EDTA, pH 6.0, buffer was placed in a vial and cooled in an ice-water bath. With good stirring, 100 ml of a dimethylformamide solution of N-(4-(N'-maleimidomethyl)cyclohexane-1-carboxyl) 3,3',5-triiodo-L-thyronine 1 mg, was added over 67 minutes. The resulting mixture was stirred at room temperature for an additional hour. Reaction of an aliquot with 5,5'-dithiobis(2-nitrobenzoic acid) indicated that reaction was complete. The conjugate was purified to remove unbound T3 by passing it through a 2.4 cm=50 cm column of Ultrogel AcA 44 eluting with the same phosphate-EDTA buffer. Tubes from the central portion of the Fab' protein peak were pooled. The ratio of Fab' protein to T3 in this conjugate is 1:1.

Example 5

Determination of Ferritin

Human serum samples were tested for ferritin. Results were read on the Immpulse® system. The assay employs the reagent prepared in Example 1. The procedure is calibrated using 4.0–50.0 ng/ml ferritin calibration standards. The assay as conducted using a manual batch procedure proceeds as follows in an illustrative determination.

Patient serum samples and calibrators, 20 μl each, were dispensed into tubes followed by 100 μl assay buffer wash using a Pipettor-Dilutor. Goat anti-ferritin antibody (1:100,000 dilution), 10 μl, was dispensed into the tubes followed by 50 μl assay buffer. The tubes were vortex mixed and incubated at 37° C. for 3 hours. The ferritin reagent of Example 1, 10 μl, was dispensed into the tubes followed by 50 μl of assay buffer. The tubes were vortex mixed and incubated at 37° C. for 30 minutes. Rabbit anti-goat Ig antibody (6:10 dilution), 10 μl, was dispensed into the tubes followed by 50 μl assay buffer wash. Polyethylene glycol solution (20%), 80 μl, was dispensed into the tubes followed by 420 μl assay buffer. The tubes were vortex mixed and incubated for 30 minutes at room temperature.

The tubes were centrifuged for 30 minutes to pellet the immune precipitate. The supernatant was decanted and measurement buffer, 500 μl, was added to dissolve the pellet, and the tubes were vortex mixed. The resulting solutions were aspirated into the flow cell of the Immpulse® fluorometer and read.

A standard curve was calculated from the relative fluorescence intensities of the calibrators. The patient sample results are determined by comparison of their fluorescence values to the standard curve.

Figure 2A:
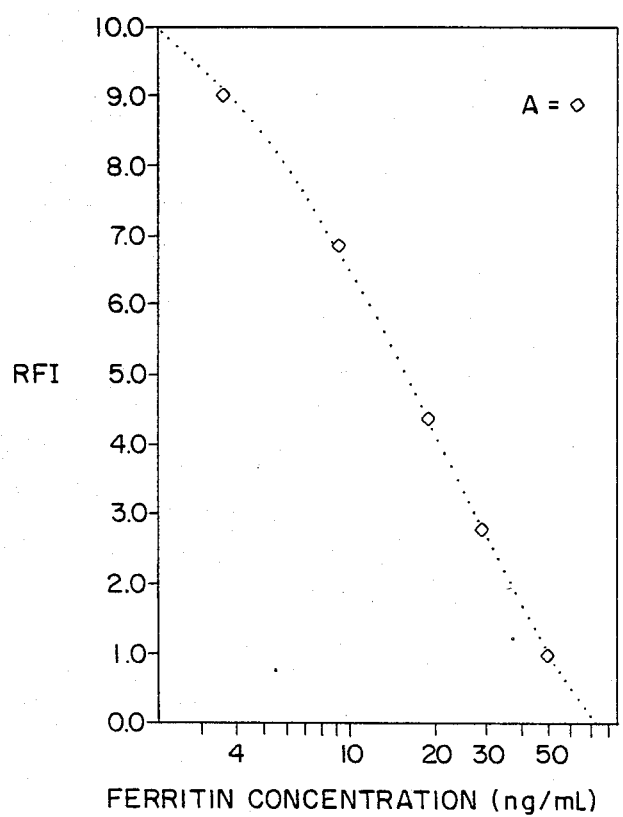
FIG. 2A shows the results of quantitation of ferritin calibration standards using the method of the invention.
Figure 2B:
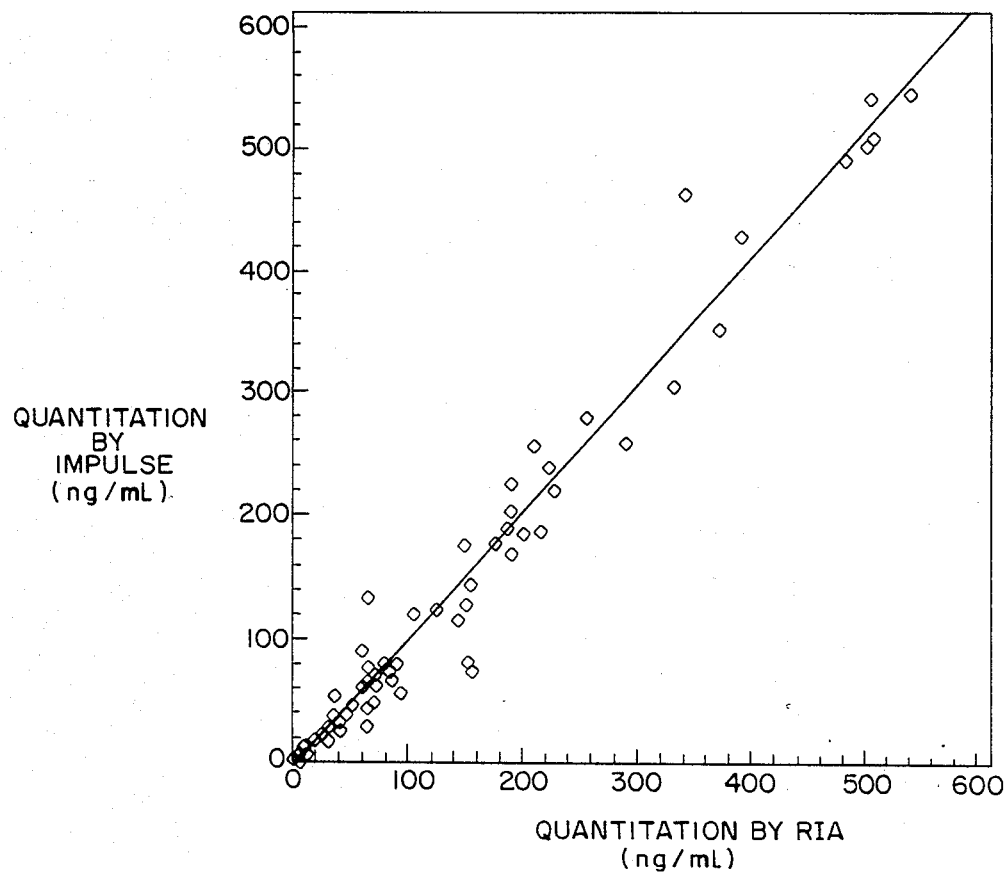
FIG. 2B shows the results of correlation of quantitation of ferritin using the method of the invention (y axis) with quantitation by RIA (x axis).

The results of the assay showing a plot of relative fluorescence intensity versus concentration in ng/ml is shown in FIG. 2A. A correlation of this study with RIA by standard methods marketed by Ramco Laboratories Inc. using 96 samples is shown in FIG. 2B. As shown in FIG. 2A, high levels of ferritin give reduced fluorescence, as the unlabeled ferritin becomes a more effective competitor. The correlation with quantitation by RIA using standards in the range of 100–600 ng/ml is shown in FIG. 2B to be substantially linear.

Example 6

Determination of IgE

In an analogous manner to that set forth above for ferritin, a manual batch procedure was conducted to determine IgE using 5.0 to 200 IU/ml calibration standards.

Patient serum samples and calibrators, 20 μl each, were dispensed into tubes followed by 100 μl assay buffer wash using a Pipettor-Dilutor. Fluorescent IgE reagent of Example 2, 10 μl, was dispensed into the tubes followed by 50 μl of assay buffer. The tubes were vortex mixed and then goat anti-IgE antibody (4:100,000 dilution). 10 μl, was dispensed into the tubes followed by 50 μl assay buffer wash. The tubes were vortex-mixed, then incubated for 4 hours at 37° C. Rabbit anti-goat Ig antibody (5:10 dilution, 10 μl) was dispensed into the tubes followed by 50 μl assay buffer wash. polyethylene glycol solution (3.2%), 500 μl, was dispensed into the tubes followed by vortex mixing and incubating for 30 minutes at room temperature. The tubes were centrifuged for 30 minutes to pellet the immune precipitate. The supernatant was decanted and measurement buffer, 566 μl, was added to dissolve the pellet and the tubes vortex mixed. The resulting solutions were aspirated into the flow cell of the Immpulse® fluorometer and read.

A standard curve is calculated from the relative fluorescence intensities of the calibrators. The patient sample results are determined by comparison of their fluorescence values to the standard curve.

Figure 3A:
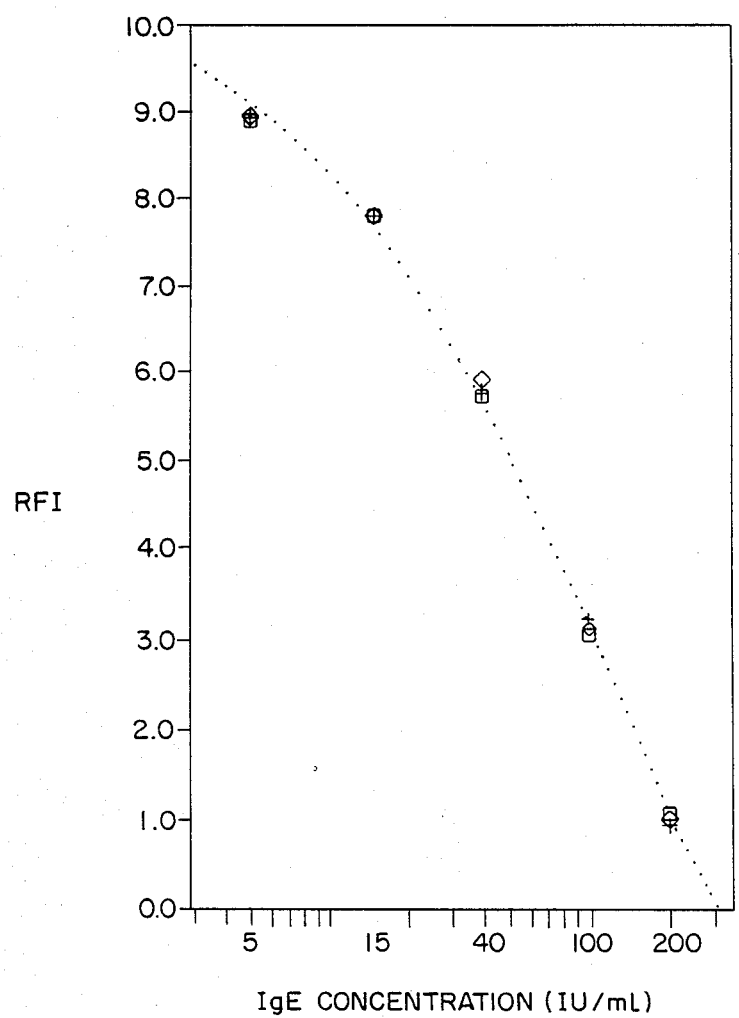
FIG. 3A shows the results of quantitation of IgE calibration standards using the method of the invention.
Figure 3B:
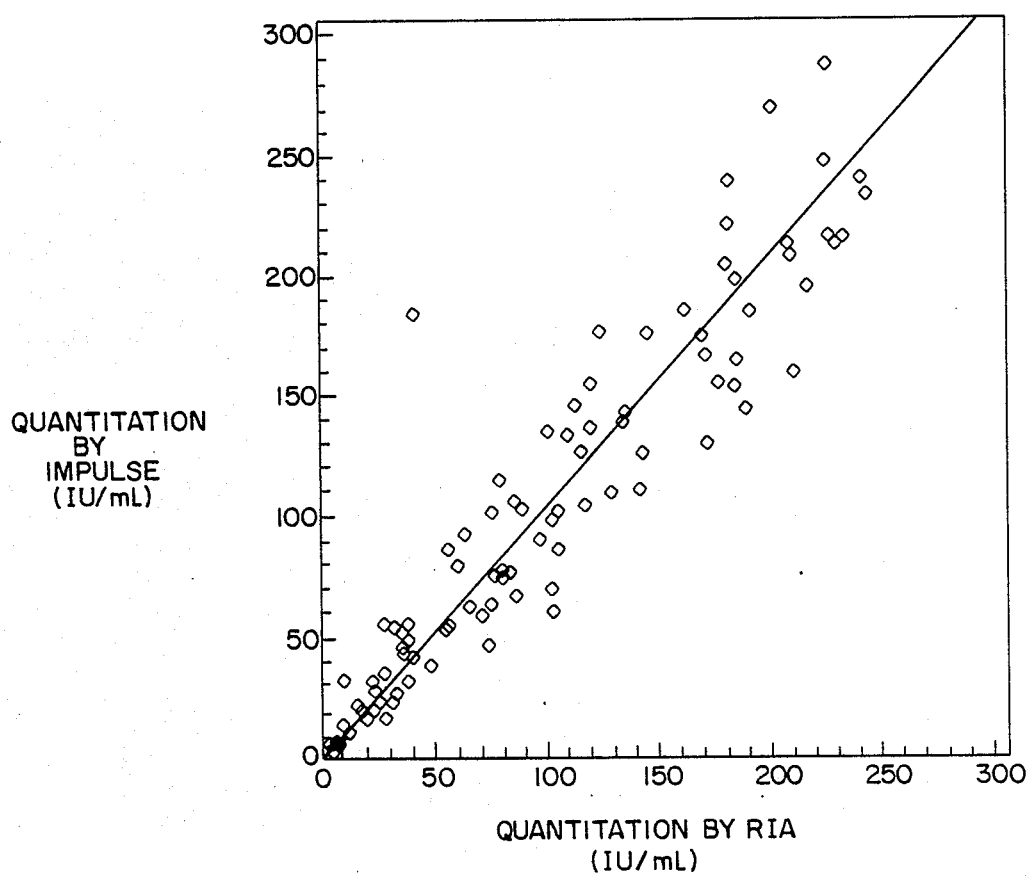
FIG. 3B shows the results of correlation of quantitation of IgE using the method of the invention (y axis) with quantitation by RIA (x axis).

Relative fluorescence intensity (RFI) results for the IgE calibration standards and correlation to RIA results for IgE patient samples are shown in FIGS. 3A and 3B.

Example 7

Determination of T3

Twenty μl serum samples, calibrators and/or controls, 20 μl of anilinonaphthalene sulfonate (13.2 mg/ml) and 20 μl of goat anti-T3 antibody solution were added into 600 μl of assay buffer containing phosphate and bovine albumin. Into the above mixture, 20 μl of the reagent of Example 4 was added, mixed, and incubated for one hour at room temperature. One hundred μl of 20% polyethylene glycol solution was then added along with 20 μl of rabbit anti-goat Ig. The mixture was centrifuged supernatant discarded and the remaining pellet dissolved in 500 μl of measurement buffer, pH 11.8. and the relative fluorescence intensity (RFI) was obtained by the Immpulse ® Fluorometer. The calibration curve is plotted, RFI vs calibrator concentration, and the unknown quantitations are obtained through interpolation.

The table below shows the relation of fluorescence to concentration of standard calibrator for the reagent of the invention and directly labeled T3.

| Calibrator | Relative Fluorescence Intensity | |
|---|---|---|
| | FITC-T3 | FITC-Fab-SMCC-T3 |
| 0.2 | 4081 | 5551 |
| 0.5 | 3911 | 4954 |
| 1.0 | 3696 | 4526 |
| 2.0 | 3448 | 3906 |
| 6.0 | 3220 | 3219 |
| Δ RFI over assay range 0.2–6.0 ng/ml | 861 | 2332 |

It should be noted that at low concentrations of calibrator the assay using the labeled T3 of the invention is much more sensitive, and that the range of RFI is greatly expanded.

We claim:

1. A method to label a specific reaction partner (SRP) useful in a binding assay, which method comprises:
    (a) conjugating label to a spacer protein selected from the group consisting of human alphal-antitrypsin, mercaptoalbumin, and fragments of rabbit IgG containing only one—SH group, which spacer protein (SP) contains only one reactive center capable of combining with one of the functional groups of a heterobifunctional linker;
    (b) reacting one of the labeled SP or the SRP with a heterobifunctional linker under conditions wherein the labeled SP or the SRP so reacted is capable of reacting with only a first functional group of the heterobifunctional linker, to obtain a product of said one of labeled SP or SRP conjugated to linker and
    (c) reacting the product of said one of labeled SP or SRP conjugated to linker with the other of the SP or SRP wherein the reaction of linker to SP employs said one reactive center.

2. The method of claim 1 wherein the label is a fluorescent label.

3. The method of claim 1 wherein the SRP is ferritin, T3, or IgE.

4. A reagent molecule for a binding assay which reagent molecule contains a multiplicity of label, and wherein the label is conjugated directly to a spacer protein (SP); selected from the group consisting of human alpha1-antitrypsin, mercaptoalbumin, and fragments of rabbit IgG containing only one—SH group which spacer protein is, in turn, conjugated to a specific reaction partner (SRP), and
    wherein each reagent molecule contains only one SRP.

5. The reagent of claim 4 wherein multiple labeled SPs are conjugated to a single SRP.

6. The reagent of claim 4 wherein each SRP is conjugated to only one labeled SP.

7. The reagent of claim 4 wherein the label is a fluorescent label.

8. The reagent of claim 7 wherein the label is fluorescein.

9. The reagent of claim 4 wherein the SRP is selected from the group consisting of ferritin, T3, or IgE.

10. The reagent of claim 8 which exhibits a fluorescence intensity, wherein the fluorescence intensity is greater than that obtained from a reagent containing a corresponding number of labeling fluorescent molecules absent the spacer protein, said fluorescence intensity having as an upper limit the total fluorescence intensity as the sum of the intensities of the labeling fluorescent molecules taken independently.

11. The reagent of claim 4 wherein the SRP is T3, the SP is rabbit IgG Fab' fragment, and the label is fluorescein.

12. The reagent of claim 11 wherein the ratio of SP:SRP is about 1:1 and the ratio of label:SP is about 2.1:1.

13. The reagent of claim 4 wherein:
    the SRP is IgE,
    the SP is rabbit IgG Fab' fragment, and the label is fluorescein.

14. The reagent of claim 11 wherein the ratio of SP:SRP is about 5.9:1 and the ratio of label:SP is about 2:1.

15. The reagent of claim 4 wherein:
    the SRP is ferritin,
    the SP is rabbit IgG Fab' fragment, and
    the label is fluorescein.

16. The reagent of claim 15 wherein the ratio of SP:SRP is about 5:1 and the ratio of label:SP is about 1.6:1.

17. A method to assay an analyte in a sample which comprises permitting the analyte in the sample to compete with a reagent which contains a multiplicity of label, said label conjugated directly to a spacer protein (SP) selected from the group consisting of human alphal-antitrypsin, mercaptoalbumin, and fragments of rabbit IgG containing only one—SH group which SP is, in turn, conjugated to a specific reaction partner (SRP), said reagent containing only one SRP residue per molecule for a complementary SRP.

18. A method to assay an analyte in a sample which comprises contacting the sample with a first SRP complementary to a second SRP, said second SRP included in a reagent which contains a multiplicity of label, said label conjugated directly to a spacer protein (SP) selected from the group consisting of human alphal-antitrypsin, mercaptoalbumin, and fragments of rabbit IgG containing only one—SH group which SP is, in turn, conjugated to said SRP, said reagent containing only one SRP residue per molecule; followed by
    contacting said first SRP with said reagent;
    separating reacted reagent from unreacted reagent;
    measuring the amount of unreacted reagent.

19. A method to assay an analyte in a sample by immunoassay which comprises treating the sample with antibody immunoreactive with said analyte;
    simultaneously or thereafter treating said antibody or immunoreactive portion thereof with a reagent which contains a multiplicity of label, said label conjugated directly to a spacer protein (SP) selected from the group consisting of human alphal-antitrypsin, mercaptoalbumin, and fragments of rabbit IgG containing only one—SH group which SP is, in turn, conjugated to a specific reaction partner (SRP), said reagent containing only one SRP residue per molecule and in which the SRP is equivalent to the analyte;

separating said reagent which has reacted with antibody from unreacted reagent; and determining the amount of reagent bound to antibody.

20. A method to label a specific reaction partner (SRP) useful in a binding assay, which method comprises:

reacting said SRP with a heterobifunctional linker having a first and second functional group under conditions wherein the SRP is capable of reacting with only a first functional group of the heterobifunctional linker so as to obtain a product of the SRP conjugated to linker, and reacting the SRP conjugated to linker with a labeled spacer protein (SP) selected from the group consisting of human alpha1-antitrypsin, mercaptoalbumin, and fragments of rabbit IgG containing only one—SH group which SP contains only one reactive center capable of combining with the second functional group of the heterobifunctional linker.

21. A method to label a specific reaction partner (SRP) useful in a binding assay, which method comprises:

reacting a labeled spacer protein (SP) selected from the group consisting of human alpha1-antitrypsin, mercaptoalbumin, and fragments of rabbit IgG containing only one—SH group with a heterobifunctional linker having a first and second functional group, which SP contains only one reactive center capable of combining with said first functional group of the heterobifunctional linker under conditions wherein the SP is capable of reacting with a first functional group of the heterobifunctional linker so as to obtain a product of the SP conjugated to linker, and treating the SP conjugated to linker with an SRP under conditions wherein the SRP reacts with the second functional group of the heterobifunctional linker.

* * * * *